United States Patent [19]
Itoh et al.

[11] Patent Number: 6,111,113
[45] Date of Patent: Aug. 29, 2000

[54] PROCESS FOR THE PREPARATION OF 2,3, 5-COLLIDINE AND 2-ETHYL-5-METHYLPYRIDINE

[75] Inventors: Naorou Itoh, Sodegaura; Nobuyuki Abe, Osaka, both of Japan

[73] Assignee: Koei Chemical Co., Ltd., Osaka, Japan

[21] Appl. No.: 09/096,383

[22] Filed: Jun. 12, 1998

[30] Foreign Application Priority Data

Jun. 16, 1997 [JP] Japan ................................. 9-176549

[51] Int. Cl.⁷ ...................... C07D 213/06; C07D 213/08; C07D 213/14
[52] U.S. Cl. ............................................ 546/251; 546/250
[58] Field of Search ..................... 546/250, 251

[56] References Cited

FOREIGN PATENT DOCUMENTS

| | | |
|---|---|---|
| 0 232 182 | 8/1987 | European Pat. Off. . |
| 0 705 821 A1 | 4/1996 | European Pat. Off. . |
| 8-245589 | 9/1996 | Japan . |
| 8-259537 | 10/1996 | Japan . |
| 97/00861 | 1/1997 | WIPO . |

OTHER PUBLICATIONS

Patent Abstracts of Japan, vol. 97, No. 2, Feb. 28, 1997 & JP 08 259537 A, Oct. 8, 1996 * abstract *.
Patent Abstracts of Japan, vol. 97, No. 1, Jan. 31, 1997 & JP 08 245589 A, Sep. 24, 1996 * abstract *.
Patent Abstracts of Japan, vol. 97, No. 9, Sep. 30, 1997 & JP 09 124602 A, May 13, 1997 * abstract *.
Patent Abstracts of Japan, vol. 10, No. 214, Jul. 25, 1986 & JP 61 053265 A, Mar. 17, 1996 * abstract *.
H. Beschke et al., "Chemiker–Zeitung" vol., 101, No. 9, Sep. 1977, pp. 377–384, XP–002076316.

*Primary Examiner*—Alan L. Rotman
*Attorney, Agent, or Firm*—Wenderoth, Lind & Ponack, LLP.

[57] ABSTRACT

2,3,5-Collidine and 2-ethyl-5-methylpyridine are prepared in high yields at the same time by reacting methacrolein and methyl ethyl ketone with ammonia in a gas phase in the presence of a catalyst which comprises silica-alumina containing at least one element selected from the group consisting of cobalt, zinc, cadmium, thallium and lead.

7 Claims, No Drawings

PROCESS FOR THE PREPARATION OF 2,3, 5-COLLIDINE AND 2-ETHYL-5-METHYLPYRIDINE

BACKGROUND OF THE INVENTION

1. Field of the Invention

The present invention relates to a process for the preparation of 2,3,5-collidine and 2-ethyl-5-methylpyridine. In particular, the present invention relates to a process for the preparation of 2,3,5-collidine and 2-ethyl-5-methylpyridine by reacting a carbonyl compound with ammonia in a gas phase in the presence of a catalyst.

2,3,5-Collidine and 2-ethyl-5-methylpyridine are useful compounds which are used in various applications such as raw materials of medicines and agrochemicals.

2. Prior Art

The following processes are known for the preparation of 2,3,5-collidine by reacting a carbonyl compound with ammonia in a gas phase in the presence of a catalyst:

- a process comprising reacting methacrolein with ammonia in a gas phase in the presence of a catalyst which comprises silicon and a specific element such as zirconium, aluminum and/or phosphorus (see JP-A-8-245589), and
- a process comprising reacting methacrolein and methyl ethyl ketone with ammonia in a gas phase in the presence of an oxide catalyst comprising silicon, phosphorus and/or boron (see JP-A-8-259537).

However, the main product of the former process is 3,5-lutidine, while 2,3,5-collidine is obtained in a yield of only 16.5%. In the latter process, 2,3,5-collidine is obtained in a yield of 15 to 37%.

However, prior arts describe neither a gas phase catalytic reaction of a carbonyl compound and ammonia for the preparation of 2-ethyl-5-methylpyridine, nor the simultaneous preparation of 2,3,5-collidine and 2-ethyl-5-methylpyridine.

SUMMARY OF THE INVENTION

One object of the present invention is to provide a process for the preparation of 2,3,5-collidine in a high yield and, at the same time, 2-ethyl-5-methylpyridine by the gas phase catalytic reaction of a carbonyl compound and ammonia.

Accordingly, the present invention provides a process for the preparation of 2,3,5-collidine and 2-ethyl-5-methylpyridine comprising reacting methacrolein and methyl ethyl ketone with ammonia in a gas phase in the presence of a catalyst which comprises silica-alumina containing at least one element selected from the group consisting of cobalt, zinc, cadmium, thallium and lead.

DETAILED DESCRIPTION OF THE INVENTION

The process of the present invention uses silica-alumina containing at least one element selected from the group consisting of cobalt, zinc, cadmium, thallium and lead, as a catalyst At least one element selected from the group consisting of cobalt, zinc, cadmium, thallium and lead is contained in the catalyst in the form of a metal, an ion and/or a compound.

Examples of the compounds of such elements are inorganic compounds such as their oxides, halides, sulfates, nitrates, hydroxides, sulfides, silicates, titanates, carbonates, etc.

The content of alumina in the silica-alumina is not limited, but is preferably between 2 and 25 wt. % of the silica-alumina.

The amount of cobalt, zinc, cadmium, thallium and/or lead is usually between 0.1 and 30 wt. %, preferably between 2 and 25 wt. %, based on the weight of the silica-alumina. The amount of such elements is the total amount of the elements in the metals, ions and compounds of such elements which are contained in the catalyst.

When the content of the alumina and the amount of the element or elements are within the above ranges, respectively, 2,3,5-collidine and 2-ethyl-5-methylpyridine are obtained in good yields, and the deterioration of the catalytic activity of the catalyst with time is suppressed.

The catalyst of the present invention may be prepared from at least one compound selected from the group consisting of inorganic compounds of the above elements (e.g. oxides, halides, sulfates, nitrates, hydroxides, sulfides, silicates, titanates, carbonates, etc.) or organometal compounds of the above elements (e.g. carboxylate salts, organic chelates, etc.) as the source materials for the elements, and a silica-alumina source such as a silica-alumina powder or a combination of a silicon compound (e.g. water glass, silica sol, alkali silicates, etc.) and an aluminum compound (e.g. aluminum nitrate, aluminum sulfate, alumina sol, etc.)

The catalyst of the present invention may be prepared by any conventional method such as impregnation, dipping, mixing, co-precipitation, ion exchange, and the like. For example, the silica-alumina powder is impregnated with the aqueous solution of the above compound(s) of the element (s), dried and calcined. The silica-alumina powder is dipped in the solution of the above compound(s) of the element(s), dried and calcined. The silica-alumina powder is mixed or kneaded with the above compound(s) of the element(s) in the form of powder and optionally with water, dried and calcined. A mixed slurry of hydroxide(s) of the element(s), silicic acid gel and aluminum hydroxide, which has been obtained from the aqueous solution of the above compound (s) of the element(s), the silicon compound and the aluminum compound, is dried and calcined. The silica-alumina powder is ion exchanged by treating the silica-alumina powder with the aqueous solution of ammonium chloride or aqueous ammonia, and then with the aqueous solution of the compound(s) of the element(s), and the silica-alumina powder containing cobalt, zinc, cadmium, thallium and/or lead ions is washed with water, dried and calcined.

In the process of the present invention, the catalyst can be used as a fixed bed catalyst or a fluidized bed catalyst.

When the catalyst of the present invention is used as the fixed bed catalyst, it is shaped in the form of a solid or hollow cylinder or a rod with a tabletting machine or an extruder, after it is optionally mixed with silica, diatomaceous earth, kaolin, bentonite, alumina and/or silica-alumina, and further with water, polyvinyl alcohol and/or vinyl acetate.

When the catalyst of the present invention is used as the fluidized bed catalyst, it is mixed with silica, diatomaceous earth, kaolin, bentonite, alumina and/or silica-alumina, and water to form a slurry, and then the slurry is spray dried to form spherical microbeads.

In either case, the shaped catalyst is calcined at a temperature of between 300 and 800° C. for several hours in the atmosphere of an air, nitrogen gas, carbon dioxide gas, etc. to strengthen the catalyst and to evaporate volatile components off. The calcination of the catalyst after shaping is not always necessary, since the catalyst is heated in a reactor for the gas-phase catalytic reaction.

The process of the present invention can be carried out by any conventional method. For example, a gaseous mixture of methacrolein, methyl ethyl ketone and ammonia is supplied over the catalyst of the present invention, and catalytically reacted in the gas phase.

The amount of methyl ethyl ketone is usually at least one mole, preferably between 1 and 5 moles per one mole of methacrolein. The amount of ammonia is usually between 0.5 and 5 moles, preferably between 1 and 3 moles, per one mole of the total of methacrolein and methyl ethyl ketone.

The gas phase catalytic reaction is preferably carried out in the presence of an inert gas such as steam or nitrogen, since side reactions are suppressed, and thus the yields of 2,3,5-collidine and 2-ethyl-5-methylpyridine increase. When the inert gas is used, its amount is usually between 0.2 and 10 moles, preferably between 0.5 and 3 moles, per one mole of the total of methacrolein and methyl ethyl ketone.

The reaction temperature for the gas phase catalyst reaction is usually in the range between 300 and 600° C., preferably in the range between 350 and 550° C. The space velocity of the mixture of the raw materials and the optional inert gas is usually between 100 and 10,000 hr$^{-1}$, preferably between 200 and 3,000 hr$^{-1}$. The reaction pressure may be reduced pressure, atmospheric pressure or elevated pressure. Preferably, the reaction pressure is between atmospheric pressure and 202 kPa (gauge pressure) (2 atm).

When the process of the present invention is performed in the form of a fixed bed, the catalyst of the present invention is packed in a reactor and heated to a reaction temperature. Then, the mixture of methacrolein, methyl ethyl ketone, ammonia and optionally an inert gas is supplied in the reactor to proceed the gas phase catalytic reaction while maintaining the suitable reaction temperature. Thus, a reaction product gas containing 2,3,5-collidine and 2-ethyl-5-methylpyridine is obtained.

The reaction product gas is condensed by cooling, or trapped in a suitable solvent. The condensed or trapped liquid containing 2,3,5-collidine and 2-ethyl-5-methylpyridine is distilled to recover 2,3,5-collidine and 2-ethyl-5-methylpyridine.

EXAMPLES

The present invention will be explained in more detail by the following examples, which do not limit the scope of the invention in any way.

Yields in the examples are molar yields based on methacrolein.

Example 1

The solution of 84 wt. parts of 30% aqueous nitric acid, 18 wt. parts of aluminum nitrate [Al(NO$_3$)$_3$•9H$_2$O] and 5 wt. parts of cadmium nitrate [Cd((NO$_3$)$_2$•4H$_2$O] in 100 wt. parts of water was mixed with the solution of 95 wt. parts of water glass (No. 3 water glass containing 29.4 wt. % of SiO$_2$) in 50 wt. parts of water which was heated at about 90° C. Then, the mixture was aged for 3 hours while maintaining pH at 8 by the addition of aqueous ammonia. The resulting precipitate was recovered by filtration, washed with water, dried, and calcined in an air at 500° C. for 5 hours. Thus, silica-alumina having an alumina content in the silica-alumina of 15 wt. % and containing cadmium oxide in an amount of 5.5 wt. % in terms of cadmium (based on the weight of the silica-alumina) was obtained.

The obtained catalyst was used in the following reaction for the preparation of 2,3,5-collidine and 2-ethyl-5-methylpyridine.

The obtained catalyst (3 g) was packed in a glass tube reactor having an inner diameter of 12.6 mm, and the catalyst-packed part of the tube was heated to 450° C. Then, a mixture of methacrolein, methyl ethyl ketone, water and ammonia in a molar ratio of 1:3:4.3:8 were passed through the catalyst-packed part of the reactor at a space velocity of 500 hr$^{-1}$. The reaction product gas, which exited from the reactor in the first 4 hour period from the start of the reaction, was condensed by cooling, and the condensate was analyzed by gas chromatography. The yields of 2,3,5-collidine and 2-ethyl-5-methylpyridine were 45% and 22%, respectively.

The yields of 2,3,5-collidine and 2-ethyl-5-methylpyridine between 26 hours and 30 hours from the start of the reaction were 43% and 22%, respectively.

Example 2

2,3,5-Collidine and 2-ethyl-5-methylpyridine were prepared in the same manner as in Example 1 except that the molar ratio of methacrolein, methyl ethyl ketone, water and ammonia was changed to 1:2:4.3:6. The yields of 2,3,5-collidine and 2-ethyl-5-methylpyridine in the first four hour period from the start of the reaction were 41% and 18%, respectively.

Example 3

Silica-alumina having an alumina content of 15 wt. % and containing lead oxide in an amount of to 9.3 wt. % in terms of lead was prepared in the same manner as in Example 1 except that 5 wt. parts of lead nitrate [Pb(NO$_3$)$_3$] was used in place of 5 wt. parts of cadmium nitrate.

Then, 2,3,5-collidine and 2-ethyl-5-methylpyridine were prepared in the same manner as in Example 1 except that the above silica-alumina containing lead oxide was used in place of the silica-alumina containing cadmium oxide. The yields of 2,3,5-collidine and 2-ethyl-5-methylpyridine in the first four hour period from the start of the reaction were 43% and 21%, respectively.

What is claimed is:

1. A process for the preparation of 2,3,5-collidine and 2-ethyl-5-methylpyridine comprising reacting methacrolein and methyl ethyl ketone with ammonia in a gas phase in the presence of a catalyst which comprises silica-alumina containing at least one element selected from the group consisting of cadmium and lead.

2. A process according to claim 1, wherein the content of alumina in said silica-alumina is between 2 and 25 wt. %.

3. A process according to claim 1, wherein the amount of said at least one element is between 0.1 and 30 wt. % of said silica-alumina.

4. A process according to claim 1, wherein said at least one element is contained in the form of an oxide in said silica-alumina.

5. A process according to claim 1, wherein the amount of methyl ethyl ketone is at least one mole per one mole of methacrolein, and the amount of ammonia is between 0.5 and 5 moles per one mole of the total of methyl ethyl ketone and methacrolein.

6. A process according to claim 1, wherein methacrolein and methyl ethyl ketone are reacted with ammonia in the presence of an inert gas.

7. A process according to claim 6, wherein said inert gas is at least one gas selected from the group consisting of steam and nitrogen.

* * * * *